(12) United States Patent
Chiang et al.

(10) Patent No.: US 9,480,458 B2
(45) Date of Patent: Nov. 1, 2016

(54) ULTRASONIC POSITIONING DEVICE FOR EPIDURAL SPACE AND METHOD USING THE SAME

(71) Applicant: NATIONAL YANG-MING UNIVERSITY, Taipei (TW)

(72) Inventors: Hui-Hua Chiang, Taipei (TW); Shih-Pin Lin, Taipei (TW); Chien-Kun Ting, Taipei (TW); Qifa Zhou, Arcadia, CA (US); K. Kirk Shung, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 457 days.

(21) Appl. No.: 13/826,693

(22) Filed: Mar. 14, 2013

(65) Prior Publication Data
US 2013/0204133 A1 Aug. 8, 2013

Related U.S. Application Data

(62) Division of application No. 12/726,962, filed on Mar. 18, 2010, now abandoned.

(30) Foreign Application Priority Data

Oct. 30, 2009 (TW) .............................. 98136952 A

(51) Int. Cl.
| | |
|---|---|
| A61B 8/12 | (2006.01) |
| A61B 5/00 | (2006.01) |
| A61B 5/06 | (2006.01) |
| A61B 8/08 | (2006.01) |
| A61B 17/34 | (2006.01) |
| A61M 37/00 | (2006.01) |
| A61M 19/00 | (2006.01) |

(52) U.S. Cl.
CPC .................. *A61B 8/12* (2013.01); *A61B 5/061* (2013.01); *A61B 5/4839* (2013.01); *A61B 5/4893* (2013.01); *A61B 5/4896* (2013.01); *A61B 8/0841* (2013.01); *A61B 17/3401* (2013.01); *A61M 37/0092* (2013.01); *A61B 2017/3413* (2013.01); *A61M 19/00* (2013.01)

(58) Field of Classification Search
CPC  A61B 8/12; A61B 37/0092; A61B 17/3401; A61B 5/061; A61B 8/0841; A61B 5/4896
See application file for complete search history.

(56) References Cited

U.S. PATENT DOCUMENTS

| | | | |
|---|---|---|---|
| 4,887,606 A | 12/1989 | Yock | |
| 5,259,385 A | 11/1993 | Miller | |
| 5,628,734 A * | 5/1997 | Hatfalvi | ........................ 604/272 |
| 6,149,598 A | 11/2000 | Tanaka | |
| 2001/0007933 A1* | 7/2001 | Lesh et al. | ..................... 604/272 |
| 2002/0173720 A1* | 11/2002 | Seo et al. | ...................... 600/437 |
| 2005/0033177 A1 | 2/2005 | Rogers | |
| 2007/0129628 A1* | 6/2007 | Hirsh | ............................ 600/411 |

FOREIGN PATENT DOCUMENTS

| | | |
|---|---|---|
| TW | M338050 | 8/2008 |

\* cited by examiner

*Primary Examiner* — Bradley Osinski
(74) *Attorney, Agent, or Firm* — Muncy, Geissler, Olds & Lowe, P.C.

(57) ABSTRACT

An ultrasonic positioning method for real time measuring the distance between the epidural needle and the epidural space is provided. The ultrasonic positioning method at least includes a puncturing step; an advancing step; a positioning step for simultaneous detecting reflected ultrasonic signals from the ligamentum flavum (LF) and dura mater (DM); a replacement step for removing the ultrasound needle transducer and putting an injecting catheter; and an injection step for injecting an anesthetic into the epidural space via the injecting catheter.

9 Claims, 5 Drawing Sheets

ULTRASONIC POSITIONING DEVICE FOR EPIDURAL SPACE AND METHOD USING THE SAME

CROSS REFERENCE TO RELATED APPLICATION

This application is a Divisional of co-pending application Ser. No. 12/726,962, filed on Mar. 18, 2010, for which priority is claimed under 35 U.S.C. §120; and this application claims priority of Application No. 098136952 filed in Taiwan on Oct. 30, 2009, under 35 U.S.C. §119, the entire contents of all of which are hereby incorporated by reference.

FIELD OF THE INVENTION

The present invention is related to an ultrasonic positioning device for epidural space and an ultrasonic positioning method, and more particularly to a positioning device and its method by using an ultrasonic echo signal to show the location of the epidural space so as to assist an epidural needle in accurately inserting into the epidural space.

BACKGROUND OF THE INVENTION

Epidural anesthesia is an anesthesia method for injecting a local anesthetic into the epidural space to perform a reversible blocking in the spinal nerve. Nowadays, the epidural anesthesia is implemented in clinics by applying the "loss-of-resistance" method by injecting saline or air through a syringe connected to the epidural needle to confirm whether the epidural needle entering into the epidural space. Anesthesiologists rely on the feeling of the thumb pressure during the pushing of the loss-of-resistance syringe to determine the location of the epidural needle. When the epidural needle pierces through the ligamentum flavum and enters into the epidural space, air or saline in the needle would be easily injected into the epidural space under moderate pressure applied by the anesthesiologist because the resistance is disappeared. Thus, it can be confirmed whether the epidural needle is located in the epidural space. However, the mentioned method is not objective and must rely on a long-term anesthesia experience.

Recently, the positioning method for the epidural space by using a combination of the force impedance and the electrical impedance has been developed, such as a Taiwan Patent No. M338050. There are differences in the force impedances and electric impedance when the epidural needle is inserted into different subcutaneous tissues of human. By using the mentioned character of the force and electrical impedance differences, the location of the epidural needle could be determined if it is inserted into the epidural space. However, the distance between the epidural needle and the epidural space can not be reported by the above method.

U.S. Pat. Nos. 4,887,606 and 5,259,385 disclose a needle for positioning the blood vessel, and these patents apply a Doppler ultrasound to position the blood vessel. However, the Doppler ultrasound positioning method is not suitable for positioning the epidural space.

Although most current methods can indeed confirm the location of the epidural needle in the epidural space, by measuring the pressure change or electric impedance change. However, those methods can not tell the distance between the epidural needle and the epidural space before the needle reaches the epidural space. Thus, it is needed for a technique which can measure the distance in real time and therefore can alert the anesthesiologist to carefully advance the needle when it nears the epidural space, and avoid the accidental dural puncture, which causes severe headache in most patients.

SUMMARY OF THE INVENTION

It is considered all previous methods only confirm the entering of the epidural needle into the epidural space; they can not report the distance between the epidural needle and the epidural space in advance. Therefore, a main purpose of the present invention is to provide a positioning device and its method for showing the location of the epidural space in real time to assist or guide the insertion of the epidural needle into the epidural space.

Therefore, in one aspect of the present invention, it is provided an ultrasonic positioning device for measuring the distance between the epidural needle and the epidural space, at least comprising:
  an epidural needle having a hollow interior;
  an ultrasound needle transducer disposed into the hollow interior of the epidural needle and connected to an ultrasonic driving device; and
  a loss-of-resistance checking syringe connected to the epidural needle for determining whether the epidural needle is inserted into the epidural space.

The mentioned ultrasonic positioning device is used by inserting the ultrasound needle transducer into the epidural needle to measure the distance between the tip of the epidural needle and the epidural space through an ultrasonic echo signal. Furthermore, the loss-of-resistance checking syringe is applied to confirm whether the epidural needle is inserted into the epidural space as a double check.

The mentioned epidural needle includes a needle tube and a connecting cylinder, as shown in FIG. 1. The needle is preferably a Tuohy needle. The connecting cylinder includes a syringe receptacle disposed at a side thereof for connecting the loss-of-resistance checking syringe. Further, the connecting cylinder includes a probe receptacle disposed on the top of the connecting cylinder for inserting the ultrasound needle transducer.

The mentioned ultrasound needle transducer could be any type for being inserted into the epidural needle. In one embodiment, the ultrasound needle transducer can be designed to have a flat facet. In another embodiment, the ultrasound needle transducer can be designed to have an oblique facet, preferably with an angle of about 45 degree.

There is preferably a probe fastening mechanism between the ultrasound needle transducer and the connecting cylinder for fixing the ultrasound needle transducer onto the connecting cylinder. The mentioned probe fastening mechanism could be any conventional fastening mechanism, such as a screwing mechanism, an engaging mechanism, or a tenoning mechanism, and is preferably the engaging mechanism or the tenoning mechanism (referring to FIGS. 1 and 2).

The mentioned loss-of-resistance checking syringe could be the conventional syringe or a similar component, element or structure. The loss-of-resistance checking syringe is connected to the connecting cylinder by any conventional connecting types, such as screwing, engaging or fitting, preferably by fitting (referring to FIGS. 1 and 2).

In another aspect, the present invention further provides an ultrasonic positioning method for guiding the epidural needle into the epidural space, it includes the steps of:
  a puncturing step which an ultrasound needle transducer is placed in an epidural needle, and the epidural needle with the ultrasound needle transducer is obliquely pierced into the joint between two vertebras through the skin.

an advancing step which the epidural needle with the ultrasound needle transducer is advanced toward the epidural space;

a positioning step which an ultrasonic echo signal is detected by the ultrasound needle transducer and showing whether the epidural needle is inserted into the epidural space in time by the ultrasonic echo signal;

a confirmation step which loss-of-resistance is conducted to determine whether the epidural needle has been inserted into the epidural space, referring to the below embodiment.

a replacement step which the ultrasound needle transducer is removed and an injecting catheter is disposed therein; and an injection step which an anesthetic is injected into the epidural space via the injecting catheter.

The preferred embodiment could be referred to the flow chart in FIG. 3.

The mentioned advancing and positioning steps could be implemented alternately or synchronously until the epidural needle is inserted into the epidural space.

The mentioned injection step is similar to the conventional injecting method, such as an anesthetic is injected into the epidural space via an injecting catheter.

The definition and the connection relationship for the ultrasound needle transducer, the epidural needle and the loss-of-resistance checking syringe used in the mentioned steps would be referred to the above.

The mentioned injecting catheter is any known injecting catheter and is preferably an epidural catheter.

The mentioned ultrasonic echo signal is displayed on an A-mode (Amplitude mode).

The details and the embodiments in the present invention are set forth in the following detailed description taken in conjunction with the accompanying drawings

DETAILED DESCRIPTION OF THE PREFERRED EMBODIMENTS

Figure 1:
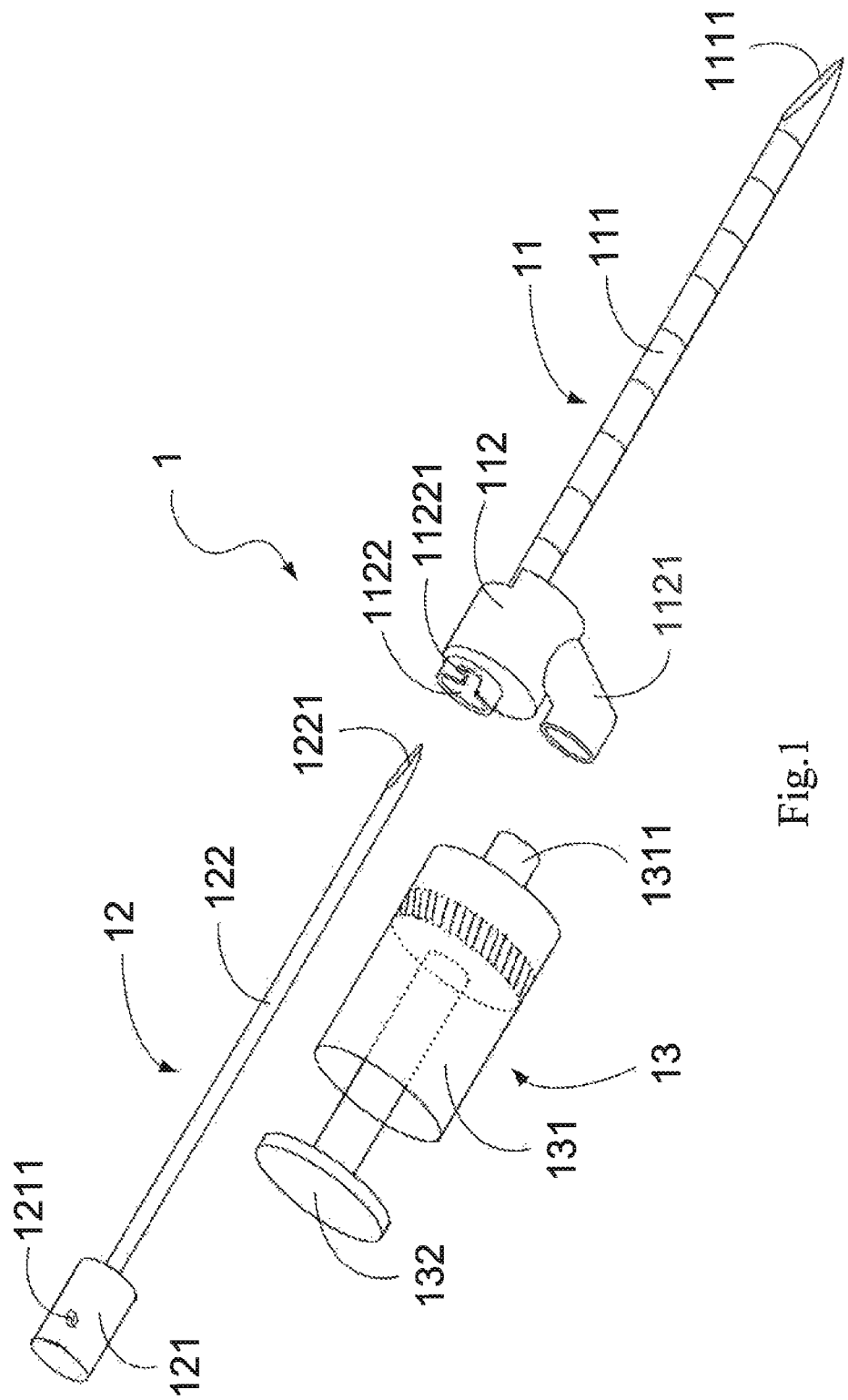
FIG. 1 is an exploded view of the present invention.
Figure 2:
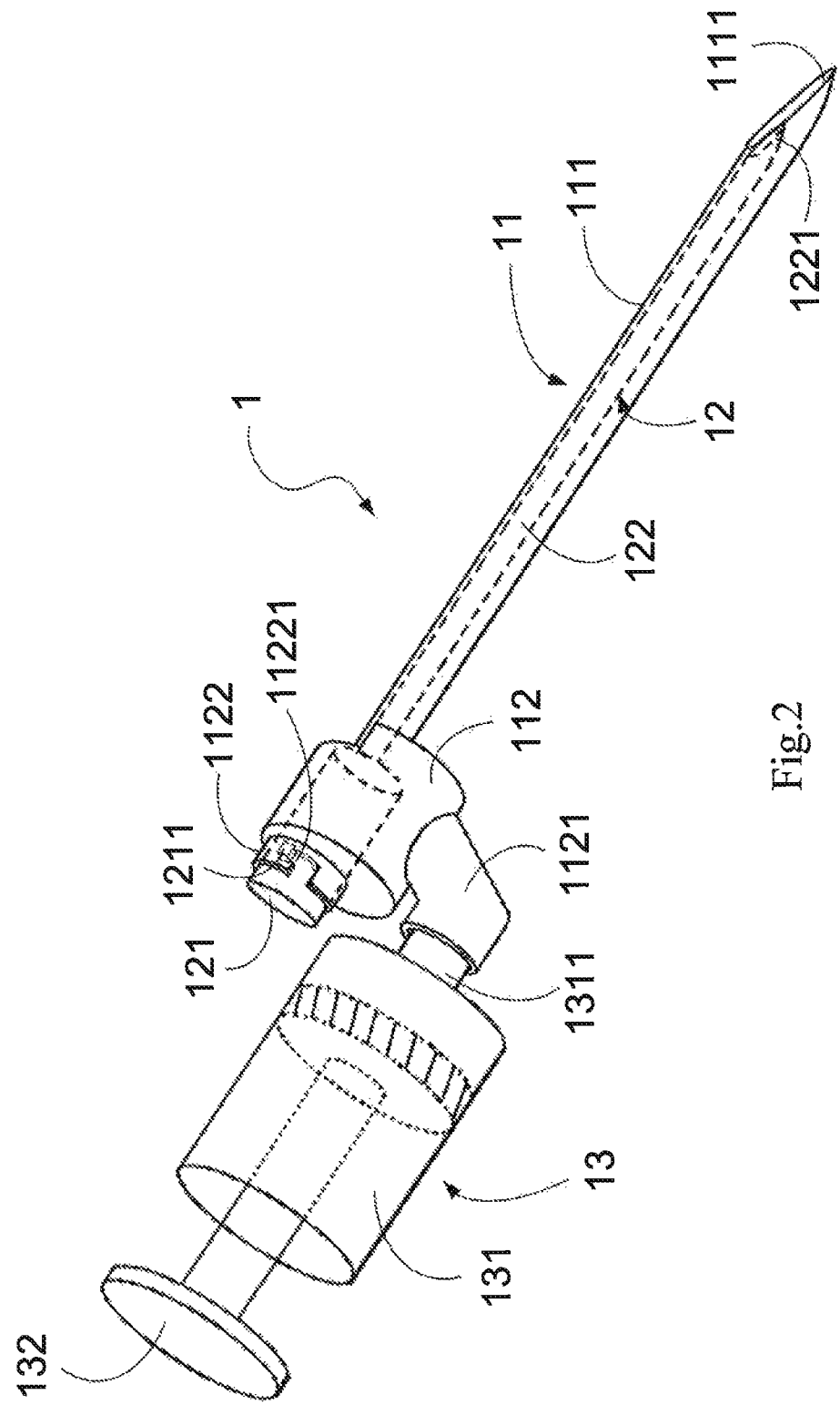
FIG. 2 is a combination view of the present invention.

Please refer to FIGS. 1 and 2, which are the exploded and combination views of the present invention. The ultrasonic positioning device of the present invention for the epidural space 1 at least includes an epidural needle 11, a connecting cylinder 12 and a loss-of-resistance checking syringe 13.

The epidural needle 11 has a hollow interior. The epidural needle 11 at least includes a needle tube 111 and a connecting cylinder 112. The needle tube 111 has a hollow interior, and the needle tube 111 has a top for connecting to the bottom of the connecting cylinder 112. A syringe receptacle 1121 is disposed at the side thereof for connecting the loss-of-resistance checking syringe. A probe receptacle 1122 is disposed on the top of the connecting cylinder 112 and a tenon trough 11221 is disposed on the side of the probe receptacle 1122.

The ultrasound needle transducer 12 is disposed on the hollow interior of the epidural needle 1. The ultrasound needle transducer 12 at least includes a probe junction 121 and a probe tube 122. The probe junction 121 is electrically connected to an external ultrasonic driving device (not shown). There is a tenon 1211 disposed on the middle of the side of the probe junction 121 for engaging with the tenon trough 11221 of the probe receptacle 1122. Thus, a probe fastening (tenoning) mechanism between the tenon trough 11221 and the tenon 1211. The bottom of the probe junction 121 would be connected to the top of the probe tube 122. There is a probe sensing end 1221 at the bottom of the probe tube 122, and there is an ultrasonic sensor (not shown) in the probe sensing end 1221. The ultrasonic sensor is used for measuring the distance between a needle head 1111 and the epidural space and transferring the measured echo signal to the external ultrasonic device.

The ultrasound needle transducer can be designed to have two types of front facet. One design is with the flat facet; the other design is with a 45 degree oblique facet. The design of the flat facet is most easy approach. The oblique facet design will need to have a good match to the aperture of the Tuohy needle tip. Since the epidural needle is obliquely inserted into the back of the patient, therefore, the design of the oblique facet will have the emitted ultrasound waves close to perpendicularly hit the tissue layer of ligamentum flavum and dura mater. Therefore, there will be a stronger reflected ultrasound signal reflected from the ligamentum flavum and dura mater.

The loss-of-resistance checking syringe 13 is connected to the epidural needle 11 for determining whether the epidural needle 11 is inserted into the epidural space. The loss-of-resistance checking syringe 13 includes a sleeve 131 and a push rod 132. The back end of the push rod 132 is fitted in the sleeve 131, whereby the push rod 132 is moved forward and backward in the sleeve 131. There is a syringe junction 1311 on the front-end of the sleeve 131 and the syringe junction 1311 is inserted into the syringe receptacle 1121.

Figure 3:
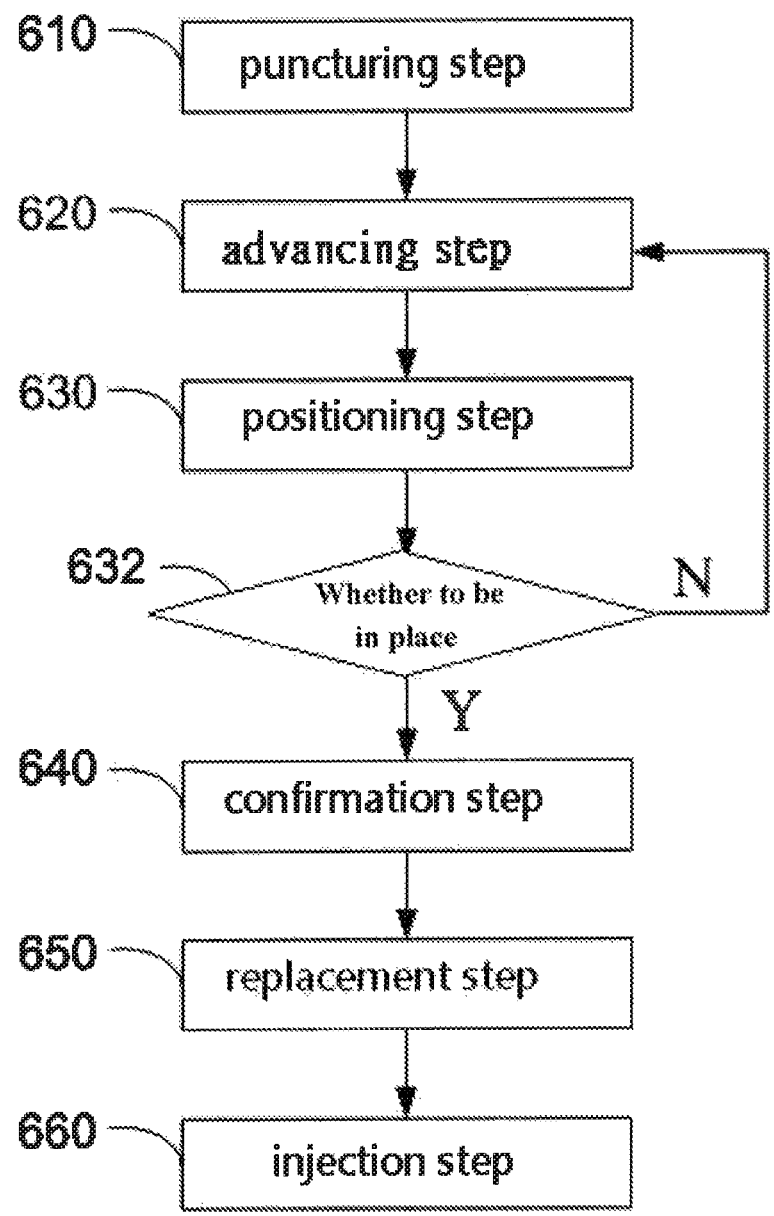
FIG. 3 is a flow chart showing the ultrasonic positioning method for the epidural space according to the preferred embodiment of the present invention.

Referring to FIG. 3, which is a flow chart of the ultrasonic positioning method for the epidural space according to the present invention. The reference numeral "610" is a puncturing step, the reference numeral "620" is an advancing step, and the reference numeral "630" is a positioning step, as disclosed above. The reference numeral "632" is an actual implementation for the step 630. If the positioning step 630 is confirmed to not be in place (the tip of the epidural needle has not been inserted into the epidural space), the advancing step 620 and the positioning step 630 will be repeatedly implemented. If the positioning step 630 is confirmed to be in place (the tip of the epidural needle has been inserted into the epidural space), a confirmation step 640 is performed (referring to the above). After the confirmation step 640, a replacement step 650 is performed (referring to the above) and then an injection step 660 is implemented (referring to the above).

Figure 4:
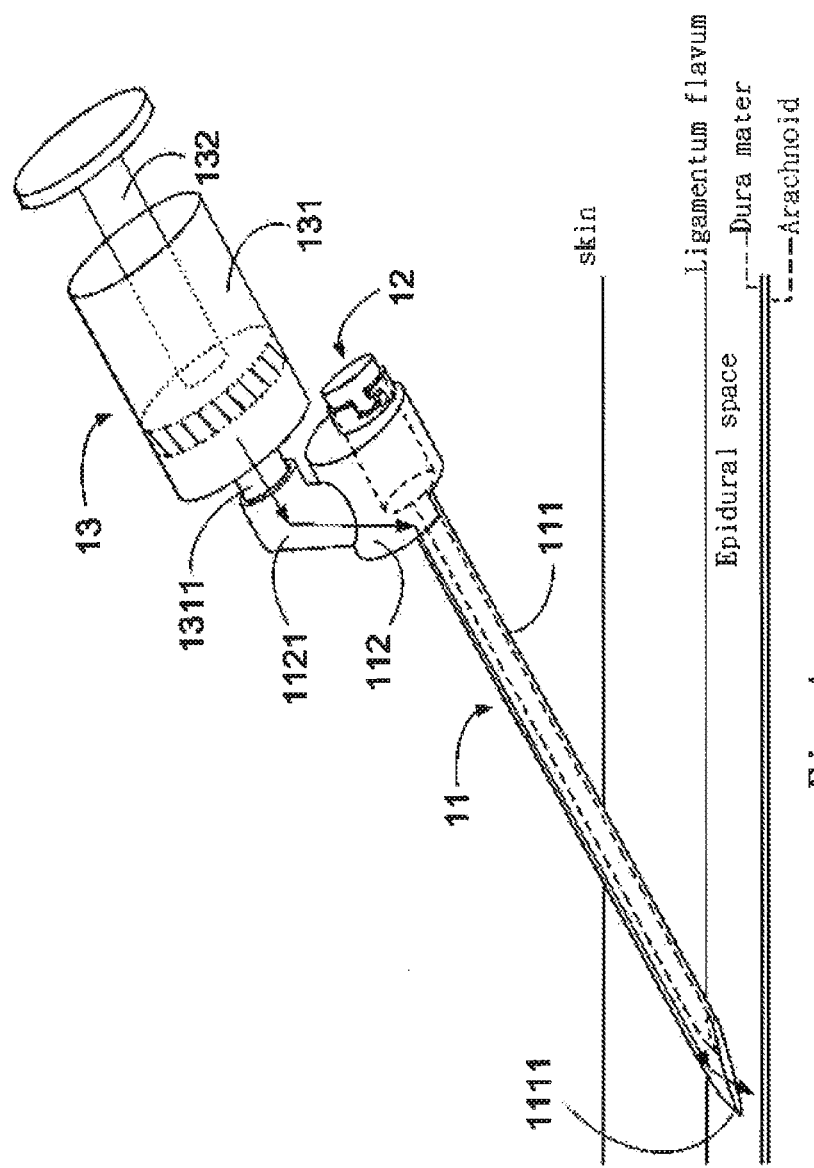
FIG. 4 is a schematic view for implementing the present invention.

FIG. 4 shows the schematic view of implementing the present invention. The ultrasound needle transducer 12 is disposed in the epidural needle 11 and the epidural needle 11 is obliquely pierced into the joint between two vertebras. Then, the epidural needle 11 is advanced toward the epidural space, the distance between the tip 1111 of the epidural needle 11 and the epidural space is measured based on the ultrasonic echo signal reflected from the ligamentum flavum and dura mater. When the ultrasonic echo signal indicates the tip of the epidural needle is inserted into the epidural space, the loss-of-resistance checking syringe 13 is pushed for determining whether the push rod 132 of the loss-of-resistance checking syringe 13 can be easily pushed. When an operator pushes the push rod 132, air or saline in the sleeve 131 is injected from the syringe junction 1311 to the syringe receptacle 1121. Then, air or saline is flowed from the receptacle 1121 to the epidural needle 11 through the connecting cylinder 112, and finally flowed to the epidural space.

If the needle is in the ligamentum flavum (LF), which is a dense tissue, the injection pressure is increased. Then, the operator would feel it is very difficult to push the push rod 132 forward. If the tip of epidural needle 11 passes through the LF and then enters into the epidural space, which is a space of negative or neutral pressure, the operator can easily pushed the push rod 132 forward and inject saline or air into the epidural space. Thus, the operator could confirm whether the tip of the epidural needle is inserted into the epidural space by this method, thereby enhancing the positioning success probability for the epidural needle.

Figure 5:
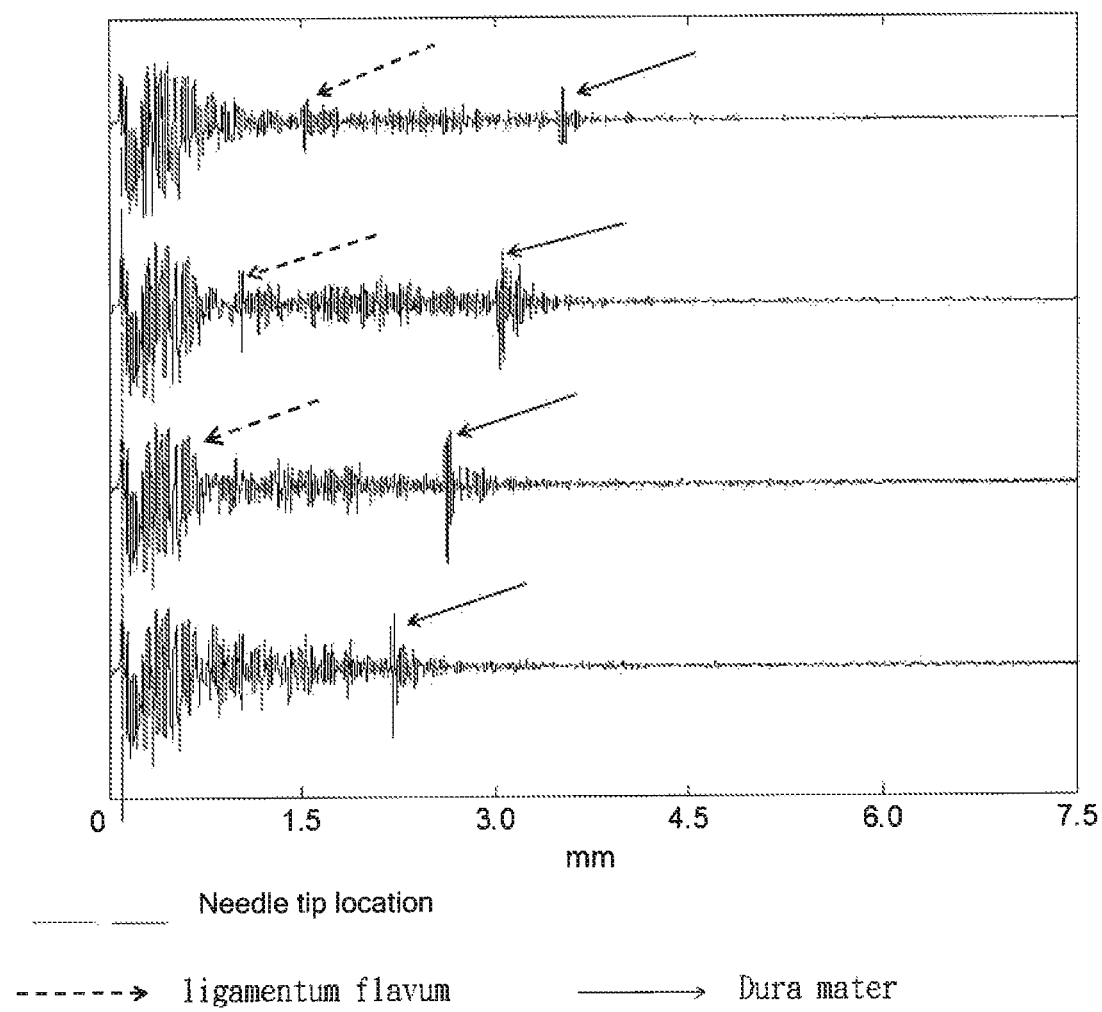
FIG. 5 is a schematic diagram illustrating the ultrasonic A-mode graph when the probe is gradually inserted into the epidural space.

FIG. 5 is an ultrasonic A-mode graph for the probe gradually advanced toward the epidural space according to the present invention. In the graph, the solid line is the location of the probe tip, the peak signal indicated by the arrow of the solid line is dura mater, and the peak signal indicated by the arrow of the dotted line is ligamentum flavum, so that epidural space is located between the dura mater and the ligamentum flavum. From top to bottom in the graph shows the probe is gradually advanced toward the epidural space, and thus the signal for the dura mater signal and the signal for the ligamentum flavum are gradually shifted towards the location of the probe tip. The bottom of the A-mode graph shows the probe tip has been inserted into the epidural space.

While the invention has been described in terms of what are presently considered to be the most practical and preferred embodiments, it is to be understood that the invention need not to be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An ultrasonic positioning method for an epidural space, comprising the steps of:
    a puncturing step for placing an ultrasound needle transducer in an epidural needle and obliquely piercing the epidural needle into a joint between two vertebras through a skin;
    an advancing step for advancing the epidural needle toward the epidural space;
    a positioning step for simultaneously detecting reflected ultrasonic signals from the ligamentum flavum (LF) and dura mater (DM), monitoring a synchronous shift of the signals for LF and DM towards the tip of the epidural needle, and determining whether a tip of the epidural needle is inserted into the epidural space by the disappearance of the LF signal;
    a replacement step for removing the ultrasound needle transducer and putting an injecting catheter; and
    an injection step for injecting an anesthetic into the epidural space via the injecting catheter, wherein
    the ultrasound needle transducer includes a facet, and
    the facet of the ultrasound needle transducer and an aperture of epidural needle are obliquely configured at a predetermined angle such that when the epidural needle is obliquely pierced into the skin and advanced toward the epidural space, the ultrasonic signals emitted from the ultrasound needle transducer substantially perpendicularly hit a tissue layer of the ligamentum flavum and the dura mater.

2. The ultrasonic positioning method of claim 1, wherein the ultrasonic signal is displayed by a radial frequency signal directly.

3. The ultrasonic positioning method of claim 1, wherein the ultrasonic signal is displayed on an A-mode.

4. The ultrasonic positioning method of claim 1, wherein the epidural needle at least comprises:
    a needle tube having a hollow interior for inserting the ultrasound needle transducer; and
    a probe fastening mechanism for fixing and releasing the ultrasound needle transducer inside the epidural needle.

5. The ultrasonic positioning method of claim 4, wherein the probe fastening mechanism is one of an engaging mechanism and a tenoning mechanism.

6. The ultrasonic positioning method of claim 1, wherein the epidural needle is a Tuohy needle.

7. The ultrasonic positioning method of claim 1, wherein the simultaneous ultrasonic signals reflected from the ligamentum flavum (LF) and dura mater (DM) are used to assist an operator to determine the entering of the tip of the epidural needle into the epidural space by the disappearance of the LF signal.

8. The ultrasonic positioning method of claim 1, further comprising a confirmation step to confirm that the tip of the epidural needle is inserted into the epidural space, which is performed by a loss-of-resistance checking syringe connected to the epidural needle.

9. The ultrasonic positioning method of claim 1, wherein the predetermined angle, at which the facet of the ultrasound needle transducer and an aperture of epidural needle are configured, is 45 degrees.

* * * * *